ized at the Surface of HBcAg Particles by Scanning with Monoclonal Antibodies," *Virology*, vol. 202, No. 2, Aug. 1, 1994, pp. 912-920.

(12) United States Patent
Maki et al.

(10) Patent No.: US 7,323,331 B2
(45) Date of Patent: Jan. 29, 2008

(54) METHOD FOR DETECTING OR ASSAYING HBV

(75) Inventors: Noboru Maki, Wako (JP); Tatsuji Kimura, Wako (JP); Yoko Oda, Wako (JP); Shintaro Yagi, Wako (JP)

(73) Assignee: Advanced Life Science Institute, Inc., Saitama (JP)

( * ) Notice: Subject to any disclaimer, the term of this patent is extended or adjusted under 35 U.S.C. 154(b) by 0 days.

(21) Appl. No.: 10/343,324

(22) PCT Filed: Aug. 10, 2001

(86) PCT No.: PCT/JP01/06947

§ 371 (c)(1),
(2), (4) Date: Feb. 6, 2003

(87) PCT Pub. No.: WO02/14871

PCT Pub. Date: Feb. 21, 2002

(65) Prior Publication Data

US 2004/0170953 A1   Sep. 2, 2004

(30) Foreign Application Priority Data

Aug. 11, 2000  (JP) ............................... 2000-249202

(51) Int. Cl.
| C12N 5/00 | (2006.01) |
| C12N 5/06 | (2006.01) |
| C12N 5/12 | (2006.01) |
| C12N 5/18 | (2006.01) |
| C12N 5/20 | (2006.01) |
| C12Q 1/00 | (2006.01) |
| C12Q 1/70 | (2006.01) |
| G01N 33/53 | (2006.01) |
| C07K 16/08 | (2006.01) |

(52) U.S. Cl. ........................... 435/339; 435/5; 435/7.1; 435/325; 435/326; 435/346; 530/388.1; 530/388.2

(58) Field of Classification Search .................... 435/5, 435/7.1, 7.2, 7.9, 7.92, 7.94, 326, 331, 332, 435/339; 530/350, 387.1, 388.1, 388.2, 388.3, 530/389.1, 389.4, 391.1; 436/518
See application file for complete search history.

(56) References Cited

U.S. PATENT DOCUMENTS 4,639,425 A   1/1987  Baier

| 4,683,136 A | * | 7/1987 | Milich et al. ............ 424/189.1 |
| 4,758,507 A | * | 7/1988 | Murray et al. .................. 435/5 |
| 4,818,527 A |   | 4/1989 | Thornton et al. |
| 6,277,631 B1 |  | 8/2001 | Noah et al. |

FOREIGN PATENT DOCUMENTS

| EP | 0 139 316 A1 | * | 2/1985 |
| EP | 0 271 302 A  |   | 6/1988 |
| EP | 0 503 252 B2 |   | 9/1992 |
| EP | 0 494 825 A1 |   | 7/1995 |
| JP | 60-53846     |   | 3/1985 |
| JP | 64-25800     |   | 1/1989 |
| JP | 5-230097 A   |   | 9/1993 |
| JP | 8-050133 A   |   | 2/1996 |
| JP | 8-50133 A    |   | 2/1996 |
| JP | 9-274041     |   | 10/1997 |
| JP | 2000-506735 A |  | 6/2000 |
| WO | WO 97/35204 A1 | | 9/1997 |
| WO | WO 98/09649 A1 | | 3/1998 |

OTHER PUBLICATIONS

Bichko et al., Molecular Immunology, vol. 30 No. 3, pp. 221-231 (1993).*
Definition "quantitate," Merriam-Webster's Online Dictionary, 10th Edition, www.m-w.com.*
Tong et al., Virology, vol. 176, pp. 596-603 (1990).*
Robertson et al., Journal of Clinical Microbiology, vol. 29 No. 3, pp. 605-610 (1991).*
Apsalons et al., Archives of Virology, vol. 134 No. 3-4, pp. 393-402 (1994).*
Pushko et al., "Identification of Hepatitis B Virus Core Protein Regions Exposed or Internalized at the Surface of HBcAg Particles by Scanning with Monoclonal Antibodies," *Virology*, vol. 202, No. 2, Aug. 1, 1994, pp. 912-920.
U.S. Appl. No. 09/269,897, Advanced Life Science Institute Inc., Not available in PAIR.
Nikolai V. Naoumov et al., "Differentiation of Core Gene Products of the Hepatitis B Virus in Infected Liver Tissue Using Monoclonal Antibodies", *Journal of Medical Virology*, vol. 53, No. 2, Oct. 1997, pp. 127-138.
Tatsuji Kimura et al., "Sensitive Enzyme Immunoassay for Hepatitis B Virus Core-Related Antigens and Their Correlation to Virus Load", *Journal of Clinical Microbiology*, Feb. 2002, pp. 439-445.

* cited by examiner

*Primary Examiner*—Zachariah Lucas
(74) *Attorney, Agent, or Firm*—Foley & Lardner LLP

(57) ABSTRACT

A Method for detecting hepatitis B virus as well as a kit and a reagent therefor, comprising using a phosphate buffer that specifically binds to hepatitis B virus, for example a monoclonal antibody that specifically binds to a specific site of core-related protein of hepatitis B virus.

1 Claim, No Drawings

METHOD FOR DETECTING OR ASSAYING HBV

FIELD OF THE INVENTION

The present invention relates to a method for detecting or measuring hepatitis B virus (HBV), and to monoclonal antibody for use in the detection and the quantitation thereof, and to a hybridoma producing said monoclonal antibody

BACKGROUND ART

Post-transfusion hepatitis refers to hepatitis caused by transfusion as the name implies, and hepatitis B virus (HBV) is the first one identified as the causative virus of post-transfusion hepatitis. In HBV antigen testing, methods for detecting hepatitis B virus surface (HBs) antigen have been used in blood screening, and methods for detecting hepatitis B virus e (HBe) antigen have been commonly used as a marker for the replication of hepatitis B virus.

HBe antigen is a pre-core protein expressed by the same promoter as that for hepatitis B virus core protein (HBc antigen) constituting the HBV particle. Since this protein is aggressively produced and secreted during the replication of HBV, the amount of HBe antigen in the blood is thought to largely reflect the amount of HBV when HBe antibody is absent. However, once the production of HBe antibody is initiated, HBe antigen forms immune complex leading to the establishment of seroconversion in which HBe antibody can only be detected. In such specimens, no HBe antigen is detected and the amount of HBV is not reflected.

On the other hand, cases have been reported in which, even at the state of seroconversion indicating the quiescence of type B hepatitis, levels of alanine aminotransferase (ALT), an indicator of hepatitis activity, may vary, and since HBV DNA was detected by the polymerase chain reaction (PCR), the presence of a precore mutant was confirmed. Precore mutants mean that since a codon at position 28 of the prepro HBe protein was mutated to a stop codon, HBe antigen can no longer been produced or secreted with a result that HBe antigen has become negative. In other words, it became clear that the measurement of HBe antigen and antibody alone is not sufficient for monitoring HBV carriers.

With the spread of the nucleic acid amplification tests (NATs), attention has been given to the relationship between the amount of HBV DNA and the pathology of HBV carriers, and accordingly NATs have been primarily used for monitoring after medication with anti-viral agents.

Though nucleic acid amplification tests such as the PCR method and the TMA method are highly sensitive methods for detecting gene fragments, however, they are complicated in that they require two hours of hands-on time in extracting HBV genomic DNA from test samples in the manual method, and involve several steps of procedures. In addition, such complicated procedures increase chances of contamination, and thereby increased possibilities of false positive samples. Furthermore, technical skills are required in order to obtain quantitative values in a stable manner, and utmost attention has to be paid in the storage of test samples in order to detect biochemically unstable substances such as DNA. This makes it hard to process a large quantity of samples at one time. Though contamination measures have been improved and processing time for DNA extraction has been curtailed in recent years due to the development of automated equipment, expensive instruments are still required, and accordingly the method has not been generally used except in facilities that process a large amount of samples.

Furthermore, since the DNA primer must be in agreement with the target gene, several types of primers must be used, which poses a problem since cost per test becomes higher as compared to immunoassays.

In stead of the above methods that detect the HBV genome, methods of directly detecting HBV core antigen (HBc antigen) have been developed. Usuda et al. (Journal of Virological Methods, 72:95-103, 1998) have developed a method for detecting HBc antigen in the serum using monoclonal antibody that has specificity for HBV core (HBc) antigen, and demonstrated that it has clinical usefulness similarly to the above NAT tests that detect the viral genome. This method, however, still has problems in several points.

First, when compared to the NAT method, it is less sensitive with a detection limit of $10^5$ copies/ml in terms of the amount of HBV DNA, and therefore can not be used in serum screening or monitoring tests.

Besides, steps of processing samples for measurement are complicated and are time-consuming, which poses problems when it is to be used in applications such as screening and monitoring. Thus, for the processing of test samples (sera), multi-stage processing is required for the concentration of viral particles and the removal of serum components, including treatment with HBs polyclonal antibody (37° C., two hours), centrifugation procedure (10 minutes), supernatant removal, treatment with surfactants, alkali treatment (35 minutes), and the addition of neutralizing agents. Such processes require highly experienced technical skills, and in order to attain reproducibility, trained skills and a processing time of at least three hours are required. Furthermore, due to steps of centrifugation, supernatant removal etc., the method is refractory to automation, and makes simultaneous bulk handling difficult, and therefore it is not suitable for applications that require bulk handling from the viewpoint of processing.

Because of these problems, it has not been put into practical use in laboratory testing.

On the other hand, the HBc antigen detection system has advantages over the NAT method in the following points. Thus, since the detection process is not accompanied by an amplification procedure, it relatively tolerates contamination. Furthermore, since it detects antigen protein which is relatively stable in stead of biochemically unstable substances such as DNA, excessive care need not be taken on the storage of test samples, which permits easier transport thereof.

These features are important requirements in applications where a large number of test samples are measured as in the blood business and physical checkups. However, the disclosed Method for detecting HBc antigen is not suitable for automation because of complicated pretreatment, and cannot be used in screening or therapeutic monitoring because of low sensitivity, and therefore the method has not utilized the advantages over the NAT method to the full extent. In addition, clinically useful methods of measurement must always address the problems of sensitivity, specificity, reproducibility, ease of operation and low cost, and must be intensively developed so as to satisfy all of these.

Literature so far reports antibodies that recognize the sequence region of the amino acid Nos. shown in [ ] on HBc antigen.

[73-89]; A. Semiletov Iu et al., Bioorg Khim 20 (11), 1175-85 (1994)

[124-133], [135-147]; M. Sallberg et al., J Gen Virol 74 (Pt7), 1335-40 (1993)

[N terminal], [134-140]; V. Skrivelis et al., Scand J Immunol 37 (6), 637-43 (1993)

[2-10], [134-140], [138-154]; V. Bichko et al., Mol Immunol 30(3), 221-31 (1993)

[126-135]; M. Sallberg et al., Mol Immunol 28(7), 719-26 (1991)

[76-85]; M. Sallberg et al., J Med Virol 33(4), 248-52 (1991)

[73-85], [107-118]; G. Colucci et al., J Immunol 141(12), 4376-80 (1988)

[9-20], [78-83], [127-133], [133-145]; P. Pushko et al., Virology 202(2), 912-20 (1994)

By using these antibodies in combination with a method of pretreating test samples, it is possible to make up a system for measuring HBc antigen. However, highly sensitive and highly specific systems of measurement have not been established yet.

DISCLOSURE OF INVENTION

Although currently there are the PCR method and the TMA method in the NAT testing for HBV, they have problems that testing cost is high and besides the procedure is complicated. Furthermore, since they use a gene amplification method, they may cause false positives when the primers for amplification are not identical with the target DNA. On the other hand, immunoassays can be carried out easily and at low cost, but the currently used methods for HBe antigen as a marker for replication cannot measure HBe antigen occurring as immune complex in the presence of HBe antibody. Furthermore, though methods of measuring HBc antigen show correlation with the amount of HBV DNA, they are not put into clinical applications since the pretreatment is complicated and the sensitivity is not sufficient.

Thus, it is an object of the present invention to provide a method of measuring HBV core-related antigens (HBe and HBc antigens) even in the presence of HBV core-related antibodies (HBe and HBc antibodies), for use in screening of type B hepatitis and in monitoring in the treatment of patients with chronic hepatitis B. Thus, it is to provide a detection system for HBV core-related antigens that has sensitivity and specificity equal to the NAT testing, and that can be readily applied, with simple pretreatment, to a large scale processing system such as automation.

The present invention provides means for detecting or measuring HBV with a high sensitivity wherein HBV particles and HBV-related proteins in the blood are denatured so as to fully expose HBV core-related antigens (HBe and HBc antigens), and when antibodies to HBe and HBc antigens are present, said antibodies are inactivated, and then HBe and HBc antigens are detected and quantitated.

Thus, the present invention provides a method for measuring HBV which method comprises detecting or quantitating the presence of HBe and HBc antigens by reacting a test sample containing HBV to a probe that specifically recognizes HBe and HBc antigens.

The present invention also provides a kit for measuring the presence or absence of, a kit or a diagnostic reagent for quantitating HBV in test samples, said kit or diagnostic reagent comprising monoclonal antibody or polyclonal antibody described below for use in the above immunoassays.

The present invention further provides a hybridoma cell line selected from the group consisting of HB44 (FERM BP-7232), HB50 (FERM BP-7233), HB61 (FERM BP-7234), HB91 (FERM BP-7235) and HB114 (FERM BP-7236) which produces a monoclonal antibody suitable for use as a probe for the detection of the above HBe and HBc antigens.

The present invention further provides a monoclonal antibody produced by a hybridoma selected from the group consisting of HB44 (FERM BP-7232), HB50 (FERM BP-7233), HB61 (FERM BP-7234), HB91 (FERM BP-7235) and HB114 (FERM BP-7236).

The present invention also provides a monoclonal antibody and a polyclonal antibody, and a method of producing the same, said antibodies recognizing amino acid Nos. 31-49 (SEQ ID NO: 1) or amino acid Nos. 1-81 (SEQ ID NO: 2) of the HBV core polypeptide which have not been reported as epitopes so far.

In addition, the present invention provides a hybridoma cell line HB110 (FERM BP-7624) which produces a monoclonal antibody suitable for use as a probe for the detection of the above HBe and HBc antigens, and the monoclonal antibody produced thereby. Furthermore, the present invention provides a method for preparing and selecting an antibody having the above properties and a hybridoma which produces said antibody.

The present invention also provides a monoclonal antibody and a polyclonal antibody, and a method of producing the same, said antibodies recognizing amino acid Nos. 21-40 (SEQ ID NO: 9) of the HBV core polypeptide which have not been reported as an epitope so far.

EMBODIMENT FOR CARRYING OUT THE INVENTION

The present invention will now be explained in detail below.

HBV core-related antigens as used herein mean HBe and HBc antigens, and include fusion proteins, fragment proteins, and peptides thereof. The amino acid sequences of HBe and HBc antigens are described in SEQ ID NO: 3 and 4, respectively. In the HBc antigen (amino acid Nos. 1-183) comprising 183 amino acids, an amino acid sequence comprising 149 amino acids in the N-terminal end overlap with the HBe antigen (amino acid Nos. −10-149), and HBe antigen is said to be the precore protein of HBV. By obtaining an antibody that specifically recognizes this common region, and then combining it with a pretreatment method for test samples to construct an assay system, it becomes possible to measure HBV core-related antigens even in the presence of antibody.

First, in order to obtain the HBc antigen, a gene fragment comprising a base sequence encoding the amino acid sequence set forth in SEQ ID NO: 4 must be cloned into an expression vector. The gene fragment of interest can be prepared by separating the viral gene from the serum of HBV patients, and then by amplifying the gene of interest by PCR. Furthermore, it can be cloned into an expression vector by using a restriction enzyme site derived from a linker added during PCR and a restriction enzyme site derived from a plasmid into which the gene fragment thereof has been inserted.

Thus, as the host, prokaryotes such as *Escherichia coli* (*E. coli*), *Bacillus subtilis* and *Actinomycetes* can be used, and as the promoter, tryptophan synthase operon (trp), lactose operon (lac), λ phage PL and PR promoter can be used.

Eukaryotes such as yeast, insect cells, plant cells and animal cells can also be used as the host. As the promoter herein, there can be mentioned 3-phosphoglycerate kinase which is a common promoter for yeast etc., a promoter for glycolytic enzymes such as enolase, a promoter for alcohol dehydrogenase, a viral promoter for use in mammalian cells such as polyoma virus, an a promoter derived from adenovirus, monkey virus SV40, vaccinia virus or cytomegalovirus.

Furthermore, vectors may comprise a marker sequence that permits the phenotype selection of transformed cells, such as an ampicillin, tetracycline resistant gene and an origin of replication, a terminator, a ribosome binding site, as appropriate.

Subsequently, for *E. coli* as an example, a method is described below in which an expression vector is transformed into a host cell, and the transformant is cultured to express the HBc antigen, which is then recovered.

As the method of transformation, a common method of transformation such as the calcium chloride method may be applied. By transforming a suitable host *E. coli* with an expression vector pATtrp-HBc, a recombinant *E. coli* can be obtained.

As the method of culturing recombinant *E. coli*, it may be cultured in a commonly used nutrient-rich medium for *E. coli* such as the L medium, the YT medium and the M9-CA medium. An expression vector prepared as described above has a drug resistance gene, and accordingly when a transformed *E. coli* is to be cultured, a drug corresponding to it should preferably added in advance to the medium at a suitable concentration. For example, when a recombinant *E. coli* HB101 [pATtrp-HBC] obtained by transforming the HB101 strain as *E. coli* with an expression vector pATtrp-HBc is cultured, it is only required to add ampicillin in advance to the medium at a concentration of 20-200 µg/ml.

When the gene of interest is to be expressed, the expression is induced by allowing a promoter upstream thereof to work in a suitable method. For example, in the case the above-mentioned vector, the microorganism is cultured until the cell mass reaches a certain level in a suitable medium, and then IAA (indole acetic acid) is added to trigger gene expression. In order to effect efficient gene expression, IAA is preferably added in the early or middle phase of the logarithmic growth period. After the induction of expression, culturing is further continued to allow the microorganism to accumulate the protein of interest in the cell. For example, in the case of *E. coli* HB101[pATtrp-HBc], by culturing in an ampicillin-supplemented M9-CA medium at 37° C. for 13-16 hours, a larger amount of cell mass can be obtained, and the protein of interest can be obtained at a high yield.

Collection and purification of the protein of interest from the cells obtained by culturing may be accomplished by commonly used technologies such as ultrasonic disruption of cells, centrifugation, and various chromatographic procedures. Thus, when the protein of interest was efficiently expressed in a method as described above, many proteins form insoluble granules in the cell, whereas HBc antigen forms HBc particles in the cell. Utilizing this characteristics, after the cells are suspended in a buffer at a physiological condition such as physiological saline, the cells are disrupted by ultrasonic treatment, the crushed cells are centrifuged, and the soluble fractions are further centrifuged to harvest HBc particles. The harvested HBc particles are subjected to gel filtration, sucrose density gradient centrifugation, and dialysis to obtain a highly purified HBc antigen, which can be used as the antigen.

Monoclonal antibodies and polyclonal antibodies against HBc antigen, HBe antigen and HBV core-related antigens such as a polypeptide containing the amino acid sequences set forth in SEQ ID NO: 1 to 5 of the present invention can be readily prepared by a person skilled in the art.

Polyclonal antibodies can be prepared by immunizing animals such as rats, rabbits, goats and sheep regularly with the above HBc antigen or a polypeptide (referred to hereinafter as the present antigen) alone or as an antigen combined with BSA or KLH in a mixture with an adjuvant such as a Freund's complete adjuvant, and then by harvesting serum. In order to obtain polyclonal antibodies having a specific recognition site, there is a method in which a partial peptide of the region of interest is used as an antigen.

The preparation of monoclonal antibodies using a hybridoma is well known. For example, BALB/c mice etc. may be immunized regularly with an intraperitoneal or subcutaneous administration of the above HBc antigen or a polypeptide (referred to hereinafter as the present antigen) alone or as an antigen combined with BSA or KLH in a mixture with an adjuvant such as a Freund's complete adjuvant. When antibody titer in the blood has increased, the present antigen is administered to the tail vein as a final immunization, and then after extracting the spleen aseptically, it is subjected to cell fusion with a suitable mouse myeloma cell line to obtain a hybridoma. The present method may be performed according to the method of Kohler and Milstein (Nature 256:495-497, 1975).

The hybridoma obtained in the above method is cultured in a suitable culture medium, and then a hybridoma cell line that produces antibody specifically reacting with the present antigen may be selected and cloned. For the cloning of an antibody-producing hybridoma, the soft agar method (Eur. J. Immunol. 6:511-519, 1976) may be used in addition to the limiting dilution method. This hybridoma may be cultured in a culture medium or in the abdominal cavity of a mouse so as to produce a monoclonal antibody in the culture medium or in the ascites.

Then, the polyclonal antibody in the serum or the monoclonal antibody in the culture medium or the ascites can be purified by a method such as Protein A column chromatography. As the polyclonal antibody, it is possible to purify antibody only that reacts with a specific antigen by a method such as affinity chromatography using an antigen immobilized on a carrier, and antibody that does not react with a specific antigen can be similarly obtained.

Molecules that may be used as a probe can be prepared in addition to the above monoclonal antibodies or polyclonal antibodies. For example, recombinant antibodies etc. are described in detail in a review by Hoogenboon (Trends in Biotechnology, 15:62-70, 1997).

The monoclonal antibody or polyclonal antibody prepared according to the present invention can be used for the detection and quantitation of HBV core-related antigens as test reagents in enzyme-linked immunosorbent assay (ELISA), enzyme immuno dot assay, radioimmunoassay, agglutination-based assay, or other known immunoassays. When labeled antibodies are used for detection, labels used include fluorophores, chemiluminescenct substances, radioactive substances, enzymes and the like.

For example, when a method is used which is based on a sandwich assay system for the detection of HBV core-related antigens in the test sample, diagnostic kits used include one or more antibodies immobilized on a solid support (for example, an inner wall of a microtiter well) and one or more antibodies or fragments thereof bound with a label. Any combinations of an antibody immobilized on a solid support and a labeled antibody may be used, and a combination that provides high sensitivity and high specificity may be selected.

Solid supports used include microtiter plates, test tubes, capillaries, beads (latex particles, red blood cells, metal compounds etc.), membranes (liposomes), filters and the like made of polystyrene, polycarbonate, polypropylene, or polyvinyl.

Test samples as used herein include biological fluids such as whole blood, plasma, serum, urine, saliva and cerebrospinal fluid, tissues such as liver tissue, and the like.

According to the present invention, an important requirement is a treating method in which HBV core-related antigens in the test sample are performed without complicated procedures to a state suitable for a binding reaction with a probe, for example a monoclonal antibody. In other words, it is important to inactivate HBc antibody or HBe antibody, and to liberate efficiently HBc antigen contained in viral particles or HBe antigen bound to serum albumin etc.

Thus, it is imperative that the pretreatment in the measurement method of the present invention can not only liberate efficiently HBV core-related antigens present in the test sample but also inactivate antibody bound to HBV core-related antigens contained in the test sample. Thus, by adding a SDS-containing solution to the test sample followed by heat treatment, HBV core-related antigens are liberated and the function of HBV core-related antibodies in the test sample is destroyed.

Furthermore, in accordance with the present invention it is an important requirement to use probes that specifically bind to the denatured antigens as above. When antibodies are used as probes, it is important to find epitopes of HBV core-related antigens that persist even after such denaturing treatment, and antibodies that can cause a specific antigen-antibody reaction in the immunoassay, and combinations thereof. According to the present invention, in order to prepare antibodies that satisfy these properties, it is important to immunize antigens previously subjected to a denaturing treatment with SDS, and further to devise methods of selecting antibodies. By selecting antibodies that react in SDS-containing solutions for immobilized antigens previously subjected to denaturing processes, antibodies suitable for immunoassays of the present invention can be obtained. When antibodies are selected from these viewpoints, antibodies that recognize hitherto unreported regions are obtained. As such antibody-recognition sites, the present invention presents two regions: the region (SEQ ID NO: 1) of amino acid Nos. 31-49 and the region (SEQ ID NO: 2) of amino acid Nos. 1-81 of HBV core polypeptide. Furthermore, as such an antibody-recognition site, the present invention presents the region (SEQ ID NO: 9) of amino acid Nos. 21-40.

The usefulness of antibodies that recognize this epitope will be described in Examples, and monoclonal antibodies or polyclonal antibodies having a similar epitope can also be used. Such antibodies can be readily prepared by using as an antigen the partial peptide of the region of interest alone or in combination with a carrier protein such as KLH and BSA. It is also possible to select antibodies that only react to the region of interest by a method in which the partial peptide of the region of interest is used as an antigen for the screening of monoclonal antibodies. Polyclonal antibodies can be purified by immobilizing antigens of interest and performing affinity chromatography to obtain antibodies that only react specific antigens.

Thus, by combining a sample pretreatment method and specific probes in a condition suitable for measurement, it is possible to detect and quantitate simply and sensitively HBV core-related antigens even in the presence of HBV core-related antibodies.

Furthermore, by using the measurement method presented by the present invention, it becomes possible to prepare a kit for measuring the presence or absence of HBV in the test sample, and a kit and a diagnostic reagent for quantitating it. The measurement method of the present invention also provides means for screening and monitoring patients with HBV.

EXAMPLES

The following Examples illustrate the present invention, but it should be noted that they do not limit the scope of the claim in any way.

Example 1

Expression and Purification of HBV Core-related Antigens (A) Construction of a HBc Antigen-expressing Plasmid An expression plasmid corresponding to the HBV core region was constructed in the following manner. One hundred µl of the patient serum was mixed with 100 µl of a DNA extraction solution [1M Tris-HCl, pH 8.4, 10 µl; 250 mM EDTA, 8 µl; 10% SDS, 40 µl; 5M NaCl, 8 µl; 20 mg/ml Proteinase K, 10 µl; tRNA (5 µg/ml), 1 µl; sterile water, 23 µl], and incubated at 54° C. for 30 minutes. Two hundred µl of phenol/chloroform (1:1) was added thereto and mixed, and after centrifugation, the supernatant was removed, to which 150 µl of isopropanol and 7 µl of 5M NaCl were added, and allowed to stand at −20° C. for 1 hour. After centrifugation at 15,000 rpm and at 4° C. for 5 minutes, the precipitate was rinsed in 70% ethanol, and centrifuged again at 15,000 rpm and at 4° C. for 5 minutes. The precipitate was air-dried, and then dissolved in 20 µl of sterile water to prepare a HBV DNA solution.

Five µl of this HBV DNA solution was subjected to PCR using two primers (5'-GAATTCATGGACATTGACCCG-TATAAA-3' (SEQ ID NO: 6), 5'-GGATCCTAACAT-TGAGATTCCCGAGA-3' (SEQ ID NO: 7)). PCR was performed using the GeneAmp™ (DNA Amplification Reagent Kit, manufactured by Perkin Elmer Cetus) at a condition of DNA denaturation at 95° C. for 1 min, annealing at 55° C. for 1 min, and DNA synthesis at 72° C. for 1 min, and the fragments obtained were separated on a 0.8% agarose gel electrophoresis, and purified by the glass powder method (GeneClean). The amplified HBc gene fragment (0.5 µg) was digested in 20 µl of a restriction enzyme solution [50 mM Tris-HCl, pH 7.5, 10 mM MgCl$_2$, 1 mM dithiothreitol, 100 mM NaCl, 15 units of EcoRI and 15 units of BamHI enzymes) at 37° C. for 1 hour, and then subjected to a 0.8% agarose gel electrophoresis to purify an about 570 bp EcoRI-BamHI fragment.

Then, 0.5 µg DNA of pATtrp, an expression vector, was digested in 20 µl of a restriction enzyme solution [50 mM Tris-HCl, pH 7.5, 10 mM MgCl$_2$, 1 mM dithiothreitol, 100 mM NaCl, 15 units of EcoRI and 15 units of BamHI enzymes) at 37° C. for 1 hour, and 39 µl of water was added to the reaction mixture, which was then heat-treated at 70° C. for 5 minutes, and 1 µl of a bacterial alkaline phosphatase (BAP) (250 units/µl) was added thereto and incubated at 37° C. for 1 hour.

By adding phenol to the reaction mixture, phenol extraction was performed, and the aqueous phase obtained was precipitated with ethanol, and the precipitate was dried. To 0.5 µg of the EcoRI-BamHI treated vector DNA obtained, the above-mentioned 570 bp HBc fragment, 5 µl of a 10× ligase buffer [660 mM Tris-HCl, pH 7.5, 66 mM MgCl$_2$, 100 mM dithiothreitol, 1 mM ATP] and 1 µl of T4 ligase (350 units/µl), water was added to make 50 µl, which was incubated overnight at 16° C. to perform a ligation reaction. In order to obtain an expression plasmid pATtrp-HBc, this ligation mixture was used to transform E. coli HB101.

The sensitive E. coli strain used for transformation can be created by the calcium chloride method [Mandel, M. and Higa, A., J. Mol. Biol., 53:159-162 (1970)]. The transformed E. coli was plated onto a LB plate (1% trypton, 0.5% NaCl, 1.5% agar) containing 25 µg/ml ampicillin, and incubated overnight at 37° C. From the microbial colony formed on the plate, one platinum loopful was taken, and transferred to the LB medium containing 25 µg/ml ampicillin, and cultured at 37° C. overnight.

1.5 ml of the microbial culture was centrifuged and the cells were harvested, and then the minipreparation of a plasmid DNA was performed by the alkali method [Manniatis et al., Molecular Cloning: A Laboratory Manual, 1982]. One µg of the plasmid DNA obtained was digested in 20 µl of a restriction enzyme solution [50 mM Tris-HCl, pH 7.5, 10 MM $MgCl_2$, 1 mM dithiothreitol, 100 mM NaCl, 15 units of EcoRI and 15 units of BamHI enzymes) at 37° C. for 1 hour, and was subjected to an agarose gel electrophoresis to select a pATtrp-HBc expression plasmid that provides about 570 bp of EcoRI-BamHI fragment.

(B) Expression and Purification of a Polypeptide Encodinq HBc Antigen

An E. coli strain HB101 bearing an expression plasmid pATtrp-HBc was inoculated into 3 ml of the 2YT medium (1.6% trypton, 1% yeast extract, 0.5% NaCl) containing 50 µg/ml of ampicillin, and cultured at 37° C. for 9 hours. One ml of this culture was subcultured to 100 ml of the M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casamino acid, 0.2% glucose), and cultured at 37° C. When OD600=0.3, indole acetic acid was added to a final concentration of 40 mg/l, and was further cultured for 16 hours. This culture was centrifuged at 5,000 rpm for 10 minutes and the cells were harvested.

To the cells, 20 ml of buffer A [50 mM Tirs-HCl, pH 8.0, 1 MM EDTA, 30 MM NaCl] was added and suspended, followed by re-centrifugation to obtain 2.6 g of the expressing cells. The cells obtained were suspended into 10 ml of buffer A. After the E. coli membrane was disrupted by sonication, it was centrifuged at 12,000 rpm and at 4° C. for 30 minutes to obtain a soluble fraction containing HBc particles. The supernatant collected was centrifuged (Beckman SW28.2 rotor) at 23,000 rpm and at 4° C. for 2 hours to obtain a precipitate. The precipitate was resuspended into a Tris-EDTA buffer (50 Tris-HCl, pH 8.0, 5 mM EDTA) containing 5% sucrose. It was applied to a Sepharose CL4B (Amersham Pharmacia Biotech) column (2.6 cm×85 cm) equilibrated with a Tris-EDTA buffer containing 5% sucrose, and was eluted with the same buffer. The fractions were analyzed by SDS-PAGE, and the fractions in which the band of molecular weight 22 kDa of the HBc antigen was detected were collected. After concentrating the collected fractions by ultrafiltration (the exclusion molecular weight, 50 kDa), the concentrate was layered on a step density grandient in which a Tris-EDTA buffer containing 40% sucrose was layered, and centrifuged at 39,000 rpm and at 4° C. for 5 hours (Beckman Ty60Ti rotor). After centrifugation, fractions were taken out sequentially from the bottom, and were analyzed by SDS-PAGE. The HBc antigen was fractionated into two layers of the high density fraction and the low density fraction, each of which was collected and used as a purified HBc antigen.

(C) Construction of an Expression Plasmid for the HBe-HBc Fusion Antigen

Subsequently a plasmid for the HBe-HBc fusion antigen was constructed. Five µl of the HBV DNA solution prepared from the above serum of patients with HBV was subjected to PCR using two primers (5'-GAATTCTCCAAGCTGT-GCCTTGGGTGGCTT-3' (SEQ ID NO. 8), 5'-GGATC-CTAACATTGAGATTCCCGAGA-3' (SEQ ID NO. 7)). PCR was performed using the GeneAmpTM (DNA Amplification Reagent Kit, manufactured by Perkin Elmer Cetus) at a condition of DNA denaturation at 95° C. for 1 min, annealing at 55° C. for 1 min, and DNA synthesis at 72° C. for 1 min, and the fragments obtained were separated on a 0.8% agarose gel electrophoresis, and purified by the glass powder method (GeneClean). The amplified HBe-HBC gene fragment (0.5 µg) was digested in 20 µl of a restriction enzyme solution [50 mM Tris-HCl, pH 7.5, 10 mM $MgCl_2$, 1 mM dithiothreitol, 100 mM NaCl, 15 units of EcoRI and 15 units of BamHI enzymes) at 37° C. for 1 hour, and then subjected to a 0.8% agarose gel electrophoresis to purify an about 600 bp EcoRI-BamHI fragment.

Then, 0.5 µg DNA of pATtrpE, an expression vector, was digested in 20 µl of a restriction enzyme solution [50 mM Tris-HCl, pH 7.5, 10 mM $MgCl_2$, 1 mM dithiothreitol, 100 mM NaCl, 15 units of EcoRI and 15 units of BamHI enzymes) at 37° C. for 1 hour, and 39 µl of water was added to the reaction mixture, which was then heat-treated at 70° C. for 5 minutes, and 1 µl of a bacterial alkaline phosphatase (BAP) (250 units/µl) was added thereto and incubated at 37° C. for 1 hour.

By adding phenol to the reaction mixture, phenol extraction was performed, and the aqueous phase obtained was precipitated with ethanol, and the precipitate was dried. To 0.5 µg of the EcoRI-BamHI treated vector DNA obtained, the above-mentioned 600 bp HBc-HBe fusion antigen, 5 µl of a 10× ligase buffer [660 mM Tris-HCl, pH 7.5, 66 mM $MgCl_2$, 100 mM dithiothreitol, 1 mM ATP] and 1 µl of T4 ligase (350 units/µl), water was added to make 50 µl, which was incubated overnight at 16° C. to perform a ligation reaction. In order to obtain an expression plasmid pATtrpE-HBe-HBc, this ligation mixture was used to transform E. coli HB101.

The sensitive E. coli strain used for transformation can be created by the calcium chloride method [Mandel, M. and Higa, A., J. Mol. Biol., 53:159-162 (1970)]. The transformed E. coli was plated onto a LB plate (1% trypton, 0.5% NaCl, 1.5% agar) containing 25 µg/ml ampicillin and incubated overnight at 37° C. From the microbial colony formed on the plate, one platinum loopful was taken, and transferred to a LB medium containing 25 µg/ml ampicillin, and cultured at 37° C. overnight.

1.5 ml of the microbial culture was centrifuged and harvested, and the minipreparation of the plasmid DNA was performed by the alkali method [Manniatis et al., Molecular Cloning: A Laboratory Manual, 1982]. One µg of the plasmid DNA obtained was digested in 20 µl of a restriction enzyme solution [50 mM Tris-HCl, pH 7.5, 10 mM $MgCl_2$, 1 mM dithiothreitol, 100 mM NaCl, 15 units of EcoRI and 15 units of BamHI enzymes) at 37° C. for 1 hour, and was subjected to agarose gel electrophoresis to select a pATtrpE-HBe-HBc expression plasmid that provides an about 600 bp of EcoRI-BamHI fragment.

(D) Expression and Purification of a Polypeptide Encoding the HBe-HBc Fusion Antigen An *E. coli* strain HB101 bearing an expression plasmid pATtrpE-HBe-HBc was inoculated into 3 ml of the 2YT medium (1.6% trypton, 1% yeast extract, 0.5% NaCl) containing 50 µg/ml of ampicillin, and cultured at 37° C. for 9 hours. One ml of this culture was subcultured to 100 ml of the M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casamino acid, 0.2% glucose), and cultured at 37° C. When OD600=0.3, indole acetic acid was added to a final concentration of 40 mg/l, and was further cultured for 16 hours. This culture was centrifuged at 5,000 rpm for 10 minutes and the cells were harvested.

To the cells, 20 ml of buffer A [50 mM Tirs-HCl, pH 8.0, 1 mM EDTA, 30 mM NaCl] was added and suspended, followed by re-centrifugation to obtain 2.6 g of the expressing cells. The cells obtained were suspended into 10 ml of buffer A. After the *E. coli* membrane was disrupted by sonication, it was centrifuged to obtain an insoluble fraction containing HBe-HBc fusion antigen.

This insoluble fraction was dissolved in 3 ml of PBS containing 8M urea, 10 mM dithiothreitol and 1 mM EDTA, and was subjected to gel filtration in the presence of 6M urea on a Sephacryl S300HR column. The product of interest was eluted in the void. To 6 ml of the void fraction, 60 mg of SDS and 9 mg of dithiothreitol were added, which was then subjected to gel filtration again in the presence of 0.1% SDS on a Sephacryl S300HR column to purify the HBe-HBc fusion antigen to a near homogeneity.

For this HBe-HBc fusion antigen, protein was determined by the BCA method, and used as a standard in the detection of HBV-related antigens from the patient samples in Example 5.

Example 2

Preparation of a Hybridoma

To the polypeptide (HBc) prepared in the above method, SDS was added to a final concentration of 10%, and subjected to a denaturation treatment at 100° C. for 5 minutes. This denatured HBc antigen was diluted in 10 mM phosphate buffer, pH 7.3, (PBS) containing 0.15 M NaCl to a final concentration of 0.2-1.0 mg/ml, and then mixed with an equal volume of Freund's adjuvant, which was administered intraperitoneally at 10-20 µg to 4-6 week-old BALB/c mice. Booster immunization was performed every 2-4 weeks for a total of five times, and as a final immunization 10 µg of HBc dissolved in PBS was given to the tail vein.

On day 3 after the final immunization, the spleen was aseptically extracted from the mice, and the spleen was crumbed with scissors and a metal meshe to individual cells, and washed three times with the RPMI1640 medium. After washing three times the mouse myeloma cell line Sp2/0Ag14 at the logarithmic growth period with the RPMI1640 medium, said cells and the spleen cells were mixed at a cell count ratio of 1:5. After centrifuging at 200×g for 5 minutes, the supernatant was removed. While gently mixing the cell mass, one ml of the RPMI1640 medium containing 50% polyethylene glycol (PEG) 4000 (Merch) was slowly added, and 10 ml of the RPMI1640 medium was further added for cell fusion.

After removing PEG by centrifugation (200×g, 5 minutes), the fused cells were suspended into a RPMI1640 medium containing 10% bovine fetal serum and hypoxanthine, aminopterin, and thymidine (HAT), which was then plated on a 96-well cell culture plate. After it was cultured for about 10 days to allow only the hybridoma to grow, a portion of the supernatant was taken, and screened for wells that produce anti-HBc antibody by an ELISA method which used, as an immobilized antigen, HBc previously denatured with SDS, to obtain a hybridoma that produces monoclonal antibody having reactivity to denatured HBc. Furthermore, a similar screening was performed in the presence of SDS to select a hybridoma that produces a monoclonal antibody having the reactivity to denatured HBc even in the presence of SDS.

For the hybridomas obtained, single cloning was performed by the limiting dilution method to establish antibody-producing hybridomas. The hybridomas obtained were designated as HB44, HB50, HB61, HB91 and HB114. Five hybridomas have been deposited with the National Institute of Advanced Industrial Science and Technology (AIST) International Patent Organism depositary (IPOD); address: Tsukuba Central 6, 1-1-1 Higashi. Tsukuba, Ibaraki, Japan Jul. 19, 2000, as the accession numbers FERM BP-7232, FERM BP-7233, FERM BP-7234, FERM BP-7235 and FERM BP-7236.

Example 3

Preparation and Analysis of Monoclonal Antibodies

The hybridomas obtained by the method described in Example 2 were transplanted to the abdominal cavity of BALB/c mice which had previously received an intraperitoneal administration of pristane, and the ascites containing monoclonal antibody produced 7-14 days later were collected. From said monoclonal antibodies, IgG fractions were separated and purified on an affinity chromatography using a Protein A Sepharose column.

Using the isotype typing kit (Zymed) which uses anti-mouse Ig antibody against each isotype, the (sub)class of each monoclonal antibody was identified. As a result, HB44, HB50, HB61, HB91 and HB114 were all IgG1 and K.

In a similar manner to Example 1 (HBc(1-183)), HBc-deletion mutants, Trx-HBc(1-47), Trx-HBc(1-81), TrpE-HBC(1-106) and HBc(1-149) were constructed. Furthermore, about 20-amino acid partial peptides PHB-1 to PHB-19 corresponding to amino acid sequences, respectively, of HBV core-related antigens were synthesized. For numbering of amino acids, the N-terminal of the HBc antigen was set as 1.

Each (poly)peptide was immobilized onto a microtiter plate, and the monoclonal antibodies obtained were examined for their reactivity to each (poly)peptide and were subjected to epitope analysis.

The result is shown in FIG. 1. The result demonstrated that since the HB44 monoclonal antibody reacts to the PHB-5 peptide and does not react to any other partial peptide, it was found to be a monoclonal antibody that recognizes the region of amino acid Nos. 31-49. Similarly, since the HB91 monoclonal antibody reacts to the PHB-2 peptide and does not react to any other partial peptide, it was found to be a monoclonal antibody that recognizes the region of amino acid Nos. 1-19. Since the HB61 monoclonal antibody reacts to the PHB-14 and PHB-15 peptides and does not react to any other partial peptide, it was found to be a monoclonal antibody that recognizes the common region of amino acid Nos. 131-140. Since the HB50 monoclonal antibody reacts to the PHB-16, 17, 18, 19 peptides, and the regions are similar repeated sequences, it was estimated to recognize the region of amino acid Nos. 168-176 which shows a stronger reaction and to cross-react to PHB16, 17 containing similar sequences. Since the HB114 monoclonal antibody does not react to any of the partial peptides PHB-1 to 19 or Trx-HBc(1-47), and reacts to Trx-HBc(1-81) and polypeptides having a wider region than that, it was estimated to recognize a structural epitope present in the region of amino acid Nos. 1-81. The recognition sites of respective monoclonal antibodies are summarized in Table 2.

In accordance with the present invention, antibodies that recognize epitope present in the region of amino acid Nos. 31-49 (SEQ ID NO: 1) and structural epitope present in the region of amino acid Nos. 1-81 (SEQ ID NO: 2) have not been reported so far, and each of the HB44 monoclonal antibody and the HB114 monoclonal antibody recognizes a novel epitope.

TABLE 1

| (Poly)peptide | Amino acid No. | Monoclonal antibody | | | | |
|---|---|---|---|---|---|---|
| | | HB44 | HB50 | HB61 | HB91 | HB114 |
| PHB-1 | −10-9 | − | − | NT | − | − |
| PHB-2 | 1-19 | − | − | NT | + | − |
| PHB-3 | 11-30 | − | − | NT | − | − |
| PHB-4 | 21-40 | − | − | NT | − | − |
| PHB-5 | 31-49 | + | − | NT | − | − |
| PHB-6 | 41-60 | − | − | NT | − | − |
| PHB-7 | 51-70 | − | − | NT | − | − |
| PHB-8 | 61-80 | − | − | NT | − | − |
| PHB-9 | 71-90 | − | − | NT | − | − |
| PHB-10 | 81-100 | NT− | − | NT | NT | − |
| PHB-11 | 91-110 | − | − | − | NT | − |
| PHB-12 | 101-120 | − | − | − | NT | − |
| PHB-13 | 111-128 | − | − | − | NT | − |
| PHB-14 | 121-140 | − | − | + | NT | − |
| PHB-15 | 131-149 | − | − | + | NT | − |
| PHB-16 | 141-159 | − | + | − | NT | − |
| PHB-17 | 150-167 | − | + | − | NT | − |
| PHB-18 | 160-176 | − | + | − | NT | − |
| PHB-19 | 168-183 | − | + | − | NT | − |
| Trx-HBc (1-47) | 1-47 | NT | − | NT | + | − |
| Trx-HBc (1-81) | 1-81 | + | − | − | + | + |
| TrpE-HBc (1-106) | 1-106 | + | − | − | + | + |
| HBc (1-149) | 1-149 | + | − | + | + | + |
| HBc (1-183) | 1-183 | + | + | + | + | + |

+: Reacted,
−: Not reacted,
NT: Not tested

TABLE 2

| Clone | Subclass | Estimated recognition site (amino acid No.) |
|---|---|---|
| HB44 | IgG1 | 31-49 |
| HB50 | IgG1 | 168-176 |
| HB61 | IgG1 | 131-140 |
| HB91 | IgG1 | 1-19 |
| HB114 | IgG1 | 1-81 |

Example 4

Method for Detecting and Measuring HBV Core Antigen

Anti-HBV core antigen monoclonal antibodies HB44, HB61 and HB114 were diluted in 0.5 M NaCl, 0.1 M carbonate buffer, pH9.6, to a final concentration of 2, 1 and 1 µg/ml, respectively, and delivered into a black 96-well microtiter plate (Nunc) at 100 µl/well, and allowed to stand at 4° C. overnight. After washing the plate twice in 0.4 ml of 10 mM sodium phosphate bueer, pH 7.4, containing 0.15 M NaCl, a blocking solution (0.5% sodium casein, 3% sucrose, 150 mM NaCl, 10 mm phosphate buffer, pH 7.4) was added thereto, and the plate was further allowed to stand at room temperature for 2 hours. After removing the blocking solution, it was vacuum-dried.

To 50 µl of serum, 25 µl of the treatment solution (15% SDS, 3% CHAPS, 1% cetyltrimethylammonium bromide) was added, which was treated at 56° C. for 30 minutes, and 50 µl thereof was used as a test sample.

To the above wells, 100 µl of the reaction buffer and 50 µl of test samples were added, and were reacted overnight at room temperature.

After washing five times in 0.4 ml of the washing solution (0.05% Tween 20, 0.15 M NaCl, 10 mM sodium phosphate buffer, pH 7.4), an alkaline phosphatase (ALP)-labeled antibody HB50 was diluted to 0.5 µg/ml, which was added to wells at 100 µl/well, and then reacted at room temperature for 2 hours. After washing six times in 0.4 ml of the washing solution, 100 µl of CDP-Star solution with Emerald II (TROPIS) was added as a luminescence substrate, and reacted at room temperature for 20 minutes, and the intensity of luminescence was measured.

The result of measurement of 25 cases of hepatitis B sero conversion panel sera from BBI is shown in Table 3. For 10 cases of normal human sera that were simultaneously measured, the result was all negative. In 13 of 25 cases of type B hepatitis panel sera, HBV core antigen was positive. Although nine cases of PHJ201-04, 05, 06, 07, 08, 12, 13, 17 and 25 were positive for HBc antibody, HBV core antigen could be measured.

This revealed that by constructing an assay system by combining the monoclonal antibody of the present invention with a method of treating test samples, HBV core antigen can be simply detected and quantitated.

Example 5

Method for Detecting and Measuring HBV Core-related Antigens

Anti-HBV core antigen monoclonal antibodies HB44, HB61 and HB114 were diluted in 0.5 M NaCl, 0.1 M carbonate buffer, pH9.6, to a final concentration of 2, 1 and 1 µg/ml, respectively, and delivered into a black 96-well microtiter plate (Nunc) at 100 µl/well, and allowed to stand at 4° C. overnight. After washing the plate twice in 0.4 ml of 10 mM sodium phosphate buffer, pH 7.4, containing 0.15 M NaCl, the blocking solution (0.5% sodium casein, 3% sucrose, 150 mM NaCl, 10 mM phosphate buffer, pH 7.4) was added thereto, and the plate was further allowed to stand at room temperature for 2 hours. After removing the blocking solution, it was vacuum-dried.

To 50 µl of serum, 25 µl of the treatment solution (15% SDS, 2% Tween 60) was added, and was treated at 56° C. for 30 minutes, and 50 µl thereof was used as a test sample.

To the above wells, 100 µl of the reaction buffer and 50 µl of test sample were added and the final concentration of SDS was 1.67%, and the wells were reacted overnight at room temperature.

After washing five times in 0.4 ml of the washing solution (0.05% Tween 20, 0.15 M NaCl, 10 mM sodium phosphate buffer, pH 7.4), alkaline phosphatase (ALP)-labeled antibody HB91 was diluted to 0.5 µg/ml, which was added to wells at 100 µl/well, and then reacted at room temperature for 2 hours. After washing six times in 0.4 ml of the washing solution, 100 µl of CDP-Star solution with Emerald II (TROPIS) was added as a luminescence substrate, and reacted at room temperature for 20 minutes, and the intensity of luminescence was measured.

Some test samples were serially diluted at $10^2$-$10^7$-fold, and then similarly determined, and HBe antigen and the amount of HBV DNA by the TMA method were determined at the same time, The result of measurement of 50 cases of hepatitis B panel sera is as follows. For 27 cases of normal human sera that were simultaneously measured, the result was all negative. In 28 of 29 cases of HBV DNA-positive sera, HBV core-related antigens could be detected. And in 10 of 21 cases of HBV DNA-negative sera, HBV core-related antigens could be detected. Thus, it was shown that this method can be detected HBV with more high sensitivity than the TMA method. HBV core antigen could also be detected in HBe antibody-positive test samples.

The result of measurement of 25 cases of hepatitis B sero conversion panel sera from BBI is shown in Table 3. For 10 cases of normal human sera that were simultaneously measured, the result was all negative. In 17 of 25 cases of hepatitis B sero conversion panel sera, HBV core-related antigens was positive. Although six cases of PHJ201-13, 15, 16, 18, 21 and 25 were positive for HBe antibody and negative for HBe antigen, HBV core-related antigens could be determined.

Four test samples of hepatitis B sero conversion panel sera were serially diluted at $10^2$-$10^7$-fold, and then HBV core-related antigens, HBV DNA, and HBe antigen were each determined, and sensitivity was compared. The result is shown in Table 4. For each test sample of PHJ201-04, 07, 08 and 13, HBV DNA could be detected to $10^5$, $10^4$, $10^3$ and $10^4$-fold dilutions by the TMA method, and HBe antigen could be detected to $10^4$, $10^4$, $10^4$ and $10^3$-fold dilutions by the RIA method. In contrast, HBV core-related antigen could be detected to $10^6$, $10^5$, $10^5$ and $10^5$-fold dilutions, and was more sensitive than the HBV DNA and HBe antigen assay system in all four test samples.

This revealed that by constructing an assay system by combining the monoclonal antibody of the present invention with a method of treating test samples, HBV core antigen can be simply detected and quantitated.

TABLE 3

| Panel No. | HBc antibody Judgement | HBV core-antigen Luminescence intensity | Judgement | HBe antigen s/co | Judgement | HBe antibody s/co | Judgement | HBV core-related antigens Luminescence intensity | Judgement |
|---|---|---|---|---|---|---|---|---|---|
| PHJ201-01 | − | 383 | + | 5.7 | + | 0.5 | − | 36,260 | + |
| PHJ201-02 | − | 4,429 | + | 17.0 | + | 0.5 | − | 51,781 | + |
| PHJ201-03 | − | 39,482 | + | 73.8 | + | 0.5 | − | 702,827 | + |
| PHJ201-04 | + | 1,009,511 | + | 107.1 | + | 0.7 | − | 1,629,518 | + |
| PHJ201-05 | + | 307 | + | 1.0 | + | 0.6 | − | 8,078 | + |
| PHJ201-06 | + | 175 | + | 1.5 | + | 0.7 | − | 16,846 | + |
| PHJ201-07 | + | 541,733 | + | 200.0 | + | 0.3 | − | 1,757,217 | + |
| PHJ201-08 | + | 15,583 | + | 195.8 | + | 0.3 | − | 1,415,741 | + |
| PHJ201-09 | − | 3,443 | + | 22.3 | + | 0.6 | − | 63,189 | + |
| PHJ201-10 | + | 47 | − | 0.1 | − | 0.6 | − | 49 | − |
| PHJ201-11 | − | 835 | + | 3.6 | + | 0.5 | − | 9,630 | + |
| PHJ201-12 | + | 225 | + | 5.8 | + | 0.6 | − | 18,112 | + |
| PHJ201-13 | + | 141,991 | + | 0.1 | − | 779.3 | − | 1,578,721 | + |
| PHJ201-14 | + | 77 | − | 0.3 | − | 10.8 | + | 41 | − |
| PHJ201-15 | + | 93 | − | 0.2 | − | 2.1 | + | 170 | + |
| PHJ201-16 | + | 77 | − | 0.2 | − | >1169.0 | + | 190 | + |
| PHJ201-17 | + | 141 | − | 0.0 | − | 1.2 | + | 64 | − |
| PHJ201-18 | + | 52 | − | 0.2 | − | >1169.0 | + | 8,781 | + |
| PHJ201-19 | + | 59 | − | 0.2 | − | 32.0 | + | 74 | − |
| PHJ201-20 | + | 54 | − | 0.1 | − | >1169.0 | + | 91 | − |
| PHJ201-21 | + | 65 | − | 0.1 | − | 26.3 | + | 128 | + |
| PHJ201-22 | + | 60 | − | 0.1 | − | >1169.0 | + | 69 | − |
| PHJ201-23 | − | 57 | − | 0.2 | − | 0.5 | − | 48 | − |
| PHJ201-24 | + | 40 | − | 0.2 | − | 1.9 | + | 61 | − |
| PHJ201-25 | + | 413 | + | 0.2 | − | >1169.0 | + | 133 | + |

+: Positive,
−: Negative

TABLE 4

| Sample | Dilution factor | HBV DNA TMA method LEG/ml | HBe antigen RIA method COI | Judgement | HBV core-related antigens EIA method Luminescence intensity | Judgement |
|---|---|---|---|---|---|---|
| Normal serum | | <3.7 | 0.4 | − | 41 | − |
| PHJ201-04 | ×10E7 | <3.7 | 0.5 | − | 55 | − |
| | ×10E6 | <3.7 | 0.7 | − | 126 | + |
| | ×10E5 | 4.0 | 0.9 | − | 713 | + |

TABLE 4-continued

| Sample | Dilution factor | HBV DNA TMA method LEG/ml | HBe antigen RIA method COI | Judgement | HBV core-related antigens EIA method Luminescence intensity | Judgement |
|---|---|---|---|---|---|---|
| | ×10E4 | 4.7 | 5.3 | + | 6,055 | + |
| | ×10E3 | 5.7 | 38.0 | + | 62,898 | + |
| | ×10E2 | 6.4 | 157.5 | + | 483,609 | + |
| PHJ201-07 | ×10E7 | <3.7 | 0.5 | − | 47 | − |
| | ×10E6 | <3.7 | 0.6 | − | 58 | − |
| | ×10E5 | <3.7 | 0.7 | − | 208 | + |
| | ×10E4 | 3.9 | 2.0 | + | 1,488 | + |
| | ×10E3 | 5.2 | 15.4 | + | 16,122 | + |
| | ×10E2 | 5.7 | 96.5 | + | 187,123 | + |
| PHJ201-08 | ×10E7 | <3.7 | 0.5 | − | 44 | − |
| | ×10E6 | <3.7 | 0.5 | − | 51 | − |
| | ×10E5 | <3.7 | 0.5 | − | 157 | + |
| | ×10E4 | <3.7 | 1.6 | +− | 1,018 | + |
| | ×10E3 | 3.9 | 10.5 | + | 12,657 | + |
| | ×10E2 | 5.0 | 76.1 | + | 123,958 | + |
| PHJ201-13 | ×10E7 | <3.7 | 0.6 | − | 29 | − |
| | ×10E6 | <3.7 | 0.4 | − | 62 | − |
| | ×10E5 | <3.7 | 0.6 | − | 253 | + |
| | ×10E4 | 4.0 | 0.6 | − | 1,435 | + |
| | ×10E3 | 4.8 | 1.0 | +− | 14,899 | + |
| | ×10E2 | 5.7 | 1.8 | +− | 191,714 | + |

+: Positive,
+−: Undetermined,
−: Negative

Example 6

In a similar manner to Example 2, a HB 110 hydridomea was established, and was deposited with the National Institute of Advanced Industrial Science and Technology (AIST) International Patent Organism depositary (IPOD); address: Tsukuba Central 6, 1-1-1 Higashi, Tsukuba, Ibaraki, Japan on Jun. 7, 2001, as the accession number FERM BP-7624.

A monoclonal antibody HB110 was prepared in a similar manner to Example 3, and the (sub)class was identified and was found to be IgGl, κ.

The result of epitope analysis performed in a similar manner to Example 3 is shown in Table 5. The result indicated that since the HB110 monoclonal antibody reacts to PHB-4 peptide and does not react to any other partial peptide, it is a monoclonal antibody that recognizes the region of amino acid NOS. 21-40. The recognition sites are shown in Table 6. Antibodies that recognize the region (SEQ ID NO: 9) of amino acid Nos. 21-40 have not been reported so far, and the HB110 monoclonal antibody of the present invention recognizes a novel epitope.

TABLE 5

| (Poly)peptide | Amino acid No. | Monoclonal antibody HB110 |
|---|---|---|
| PHB-1 | −10-9 | − |
| PHB-2 | 1-19 | − |
| PHB-3 | 11-30 | − |
| PHB-4 | 21-40 | + |
| PHB-5 | 31-49 | − |
| PHB-6 | 41-60 | − |
| PHB-7 | 51-70 | − |
| PHB-8 | 61-80 | − |
| PHB-9 | 71-90 | − |
| Trx-HBc (1-47) | 1-47 | + |
| Trx-HBc (1-81) | 1-81 | + |
| TrpE-HBc (1-106) | 1-106 | + |
| HBc (1-149) | 1-149 | + |
| HBc (1-183) | 1-183 | + |

+: Reacted,
−: Not reacted

TABLE 6

| Clone | Subclass | Estimated recognition site (amino acid No.) |
|---|---|---|
| HB110 | IgG1 | 21-40 |

Example 7

Method for Detecting and Measuring HBV Core-related Antigens

In a similar manner to Example 5, HBV core-related antigens were determined. However, as alkaline phosphatase (AP)-labeled monoclonal antibody, HB110 in addition to HB91 was used. Four test samples of hepatitis B sero conversion patient panel serum of BBI were serially diluted to $10^2$-$10^7$-fold, and HBV core-related antigens, HBV DNA and HBe antigen were determined, and sensitivity was compared. The result is shown in Table 7. For each test sample of PHJ201-04, 07, 08 and 13, HBV DNA could be detected to $10^5$, $10^4$, $10^3$ and $10^4$-fold dilutions by the TMA method, and HBe antigen could be detected to $10^4$, $10^4$, $10^4$ and $10^3$-fold dilutions by the RIA method. In contrast, HBV antigen-related antigens could be detected to $10^5$, $10^5$, $10^4$ and $10^5$-fold dilutions, and was more sensitive than the HBV DNA and HBe antigen assay system.

This revealed that by constructing an assay system by combining the monoclonal antibody of the present invention with a method of treating test samples, HBV core antigen can be simply detected and quantitated.

TABLE 7

| Sample | Dilution factor | HBV DNA TMA method LEG/ml | HBe antigen RIA method COI | RIA method Judgement | HBV core-related antigens EIA method (HB91 + HB110) Luminescence intensity | Judgement |
|---|---|---|---|---|---|---|
| Normal serum | | <3.7 | 0.4 | − | 352 | − |
| PHJ201-04 | ×10E7 | <3.7 | 0.5 | − | 346 | − |
| | ×10E6 | <3.7 | 0.7 | − | 524 | − |
| | ×10E5 | 4.0 | 0.9 | − | 2,043 | + |
| | ×10E4 | 4.7 | 5.3 | + | 15,271 | + |
| | ×10E3 | 5.7 | 38.0 | + | 135,005 | + |
| | ×10E2 | 6.4 | 157.5 | + | 747,176 | + |
| PHJ201-07 | ×10E7 | <3.7 | 0.5 | − | 336 | − |
| | ×10E6 | <3.7 | 0.6 | − | 372 | − |
| | ×10E5 | <3.7 | 0.7 | − | 691 | + |
| | ×10E4 | 3.9 | 2.0 | + | 3,889 | + |
| | ×10E3 | 5.2 | 15.4 | + | 37,724 | + |
| | ×10E2 | 5.7 | 96.5 | + | 317,844 | + |
| PHJ201-08 | ×10E7 | <3.7 | 0.5 | − | 321 | − |
| | ×10E6 | <3.7 | 0.5 | − | 375 | − |
| | ×10E5 | <3.7 | 0.5 | − | 628 | − |
| | ×10E4 | <3.7 | 1.6 | +− | 2,926 | + |
| | ×10E3 | 3.9 | 10.5 | + | 25,222 | + |
| | ×10E2 | 5.0 | 76.1 | + | 202,371 | + |
| PHJ201-13 | ×10E7 | <3.7 | 0.6 | − | 358 | − |
| | ×10E6 | <3.7 | 0.4 | − | 401 | − |
| | ×10E5 | <3.7 | 0.6 | − | 749 | + |
| | ×10E4 | 4.0 | 0.6 | − | 4,444 | + |
| | ×10E3 | 4.8 | 1.0 | +− | 40,945 | + |
| | ×10E2 | 5.7 | 1.8 | +− | 315,038 | + |

+: Positive,
+−: Undetermined,
−: Negative

The invention claimed is:

1. A hybridoma cell HB44 (FERM BP-7232) which produces a monoclonal antibody having a binding specificity for a hepatitis B virus core antigen.

* * * * *

SEQUENCE LISTING

<160> NUMBER OF SEQ ID NOS: 9

<210> SEQ ID NO 1
<211> LENGTH: 19
<212> TYPE: PRT
<213> ORGANISM: Hepatitis B virus
<220> FEATURE:
<223> OTHER INFORMATION: N-terminal amino acid sequence of HBV
      core-related protein

<400> SEQUENCE: 1

Leu Asp Thr Ala Ser Ala Leu Tyr Arg Glu Ala Leu Glu Ser Pro Glu
  1               5                  10                  15

His Cys Ser

<210> SEQ ID NO 2
<211> LENGTH: 81
<212> TYPE: PRT
<213> ORGANISM: Hepatitis B virus
<220> FEATURE:
<223> OTHER INFORMATION: N-terminal amino acid sequence of HBV
      core-related protein

```
<400> SEQUENCE: 2

Met Asp Ile Asp Pro Tyr Lys Glu Phe Gly Ala Ser Val Glu Leu Leu
  1               5                  10                  15

Ser Phe Leu Pro Ser Asp Phe Phe Pro Ser Ile Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Asn Leu Ala Thr Trp Val Gly Ser Asn Leu Glu Asp Pro Ala
 65                  70                  75                  80

Ser

<210> SEQ ID NO 3
<211> LENGTH: 159
<212> TYPE: PRT
<213> ORGANISM: Hepatitis B virus
<220> FEATURE:
<223> OTHER INFORMATION: Amino acid sequence of HBe antigen

<400> SEQUENCE: 3

Ser Lys Leu Cys Leu Gly Trp Leu Trp Gly Met Asp Ile Asp Pro Tyr
  1               5                  10                  15

Lys Glu Phe Gly Ala Ser Val Glu Leu Leu Ser Phe Leu Pro Ser Asp
                 20                  25                  30

Phe Phe Pro Ser Ile Arg Asp Leu Leu Asp Thr Ala Ser Ala Leu Tyr
             35                  40                  45

Arg Glu Ala Leu Glu Ser Pro Glu His Cys Ser Pro His His Thr Ala
         50                  55                  60

Leu Arg Gln Ala Ile Leu Cys Trp Gly Glu Leu Met Asn Leu Ala Thr
 65                  70                  75                  80

Trp Val Gly Ser Asn Leu Glu Asp Pro Ala Ser Arg Glu Leu Val Val
                 85                  90                  95

Ser Tyr Val Asn Val Asn Met Gly Leu Lys Ile Arg Gln Leu Leu Trp
            100                 105                 110

Phe His Ile Ser Cys Leu Thr Phe Gly Arg Glu Thr Val Leu Glu Tyr
            115                 120                 125

Leu Val Ser Phe Gly Val Trp Ile Arg Thr Pro Pro Ala Tyr Arg Pro
        130                 135                 140

Pro Asn Ala Pro Ile Leu Ser Thr Leu Pro Glu Thr Thr Val Val
145                 150                 155

<210> SEQ ID NO 4
<211> LENGTH: 183
<212> TYPE: PRT
<213> ORGANISM: Hepatitis B virus
<220> FEATURE:
<223> OTHER INFORMATION: Amino acid sequence of HBc antigen

<400> SEQUENCE: 4

Met Asp Ile Asp Pro Tyr Lys Glu Phe Gly Ala Ser Val Glu Leu Leu
  1               5                  10                  15

Ser Phe Leu Pro Ser Asp Phe Phe Pro Ser Ile Arg Asp Leu Leu Asp
                 20                  25                  30

Thr Ala Ser Ala Leu Tyr Arg Glu Ala Leu Glu Ser Pro Glu His Cys
             35                  40                  45
```

```
Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
                180
```

```
<210> SEQ ID NO 5
<211> LENGTH: 193
<212> TYPE: PRT
<213> ORGANISM: Hepatitis B virus
<220> FEATURE:
<223> OTHER INFORMATION: HBe-HBc fusion antigen

<400> SEQUENCE: 5

Ser Lys Leu Cys Leu Gly Trp Leu Trp Gly Met Asp Ile Asp Pro Tyr
1               5                   10                  15

Lys Glu Phe Gly Ala Ser Val Glu Leu Leu Ser Phe Leu Pro Ser Asp
                20                  25                  30

Phe Phe Pro Ser Ile Arg Asp Leu Leu Asp Thr Ala Ser Ala Leu Tyr
            35                  40                  45

Arg Glu Ala Leu Glu Ser Pro Glu His Cys Ser Pro His His Thr Ala
    50                  55                  60

Leu Arg Gln Ala Ile Leu Cys Trp Gly Glu Leu Met Asn Leu Ala Thr
65                  70                  75                  80

Trp Val Gly Ser Asn Leu Glu Asp Pro Ala Ser Arg Glu Leu Val Val
                85                  90                  95

Ser Tyr Val Asn Val Asn Met Gly Leu Lys Ile Arg Gln Leu Leu Trp
                100                 105                 110

Phe His Ile Ser Cys Leu Thr Phe Gly Arg Glu Thr Val Leu Glu Tyr
            115                 120                 125

Leu Val Ser Phe Gly Val Trp Ile Arg Thr Pro Pro Ala Tyr Arg Pro
        130                 135                 140

Pro Asn Ala Pro Ile Leu Ser Thr Leu Pro Glu Thr Thr Val Val Arg
145                 150                 155                 160

Arg Arg Gly Arg Ser Pro Arg Arg Thr Pro Ser Pro Arg Arg Arg
                165                 170                 175

Arg Ser Gln Ser Pro Arg Arg Arg Ser Gln Ser Arg Glu Ser Gln
                180                 185                 190

Cys
```

```
<210> SEQ ID NO 6
<211> LENGTH: 27
<212> TYPE: DNA
```

```
<213> ORGANISM: Artificial Sequence
<220> FEATURE:
<223> OTHER INFORMATION: Description of Artificial Sequence: Primer

<400> SEQUENCE: 6
gaattcatgg acattgaccc gtataaa                                           27

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 7
ggatcctaac attgagattc ccgaga                                            26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
gaattctcca agctgtgcct tgggtggctt                                        30

<210> SEQ ID NO 9
<211> LENGTH: 20
<212> TYPE: PRT
<213> ORGANISM: Hepatitis B virus
<220> FEATURE:
<223> OTHER INFORMATION: Amino acid sequence from 21st amino acid to
      40th amino acid of HBV core-related protein

<400> SEQUENCE: 9

Ser Asp Phe Phe Pro Ser Ile Arg Asp Leu Leu Asp Thr Ala Ser Ala
 1               5                  10                  15

Leu Tyr Arg Glu
            20
```